United States Patent [19]

Rentzea et al.

[11] 4,350,701
[45] Sep. 21, 1982

[54] 1-(TRIHALOMETHYL-SULFENYL)-4-ARYL-1,2,4-TRIAZOLIN-5-ONES, AND PROCESS FOR CONTROLLING FUNGI

[75] Inventors: Costin Rentzea, Heidelberg; Bernd Zeeh, Ludwigshafen; Ernst-Heinrich Pommer, Limburgerhof; Celia J. Mappes, Westheim, all of Fed. Rep. of Germany

[73] Assignee: BASF Aktiengesellschaft, Fed. Rep. of Germany

[21] Appl. No.: 251,125

[22] Filed: Apr. 6, 1981

[30] Foreign Application Priority Data

Apr. 19, 1980 [DE] Fed. Rep. of Germany ....... 3015090

[51] Int. Cl.³ ................ A01N 43/64; A01N 47/04; C07D 249/12
[52] U.S. Cl. .................................. 424/269; 424/200; 424/248.4; 424/249; 424/250; 424/251; 424/263; 424/272; 424/273 R; 424/273 B; 106/18.32; 548/263; 548/265
[58] Field of Search ................ 548/263, 265; 424/269

[56] References Cited

U.S. PATENT DOCUMENTS

| | | | |
|---|---|---|---|
| 2,553,770 | 5/1951 | Kittleson | 424/270 |
| 2,553,773 | 5/1951 | Cohen | 424/270 |
| 3,484,451 | 12/1969 | Moon | 548/264 |
| 3,767,666 | 10/1973 | Zielinski | 548/264 |
| 3,937,713 | 2/1976 | Paget et al. | 548/263 |
| 4,098,896 | 7/1978 | Edwards | 424/269 |

OTHER PUBLICATIONS

Chemical Week, Jun. 21, 1979, p. 63.
Chemical Week, Jun. 21, 1972, p. 55.

*Primary Examiner*—Alton D. Rollins
*Attorney, Agent, or Firm*—Keil & Witherspoon

[57] ABSTRACT

1-(Trihalomethyl-sulfenyl)-4-aryl-1,2,4-triazolin-5-ones of the general formula

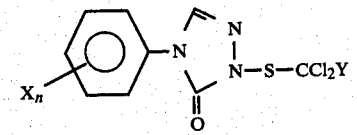

where X is hydrogen, halogen, unsubstituted or substituted alkyl or alkoxy, alkenyl, cyano, nitro or unsubstituted or substituted phenyl or phenoxy, n is an integer from 1 to 5 and Y is fluorine or chlorine, and fungicides which contain these compounds.

3 Claims, No Drawings

1-(TRIHALOMETHYL-SULFENYL)-4-ARYL-1,2,4-TRIAZOLIN-5-ONES, AND PROCESS FOR CONTROLLING FUNGI

The present invention relates to novel valuable 1-(trihalomethyl-sulfenyl)-4-aryl-1,2,4-triazolin-5-ones, having a fungicidal action, processes for their preparation, the use of the compounds for controlling phytopathogenic fungi, and fungicides which contain the novel compounds.

The use of N-trichloromethylthio-tetrahydrophthalimide for controlling phytopathogenic fungi has been disclosed (Chemical Week, June 21, 1972, page 63). However, its action against other Phycomycetes, for example Phytophthora infestans in tomatoes or potatoes, is not satisfactory. It also has an insufficient action for it to be used for the protection of materials, and for protecting timber against fungi which cause its discoloration.

The use of 2,4,5,6-tetrachloroisophthalodinitrile for controlling fungi has also been disclosed (Chemical Week, June 21, 1972, page 55).

We have found that the novel 1-(trihalomethyl-sulfenyl)-4-aryl-1,2,4-triazolin-5-ones of the general formula

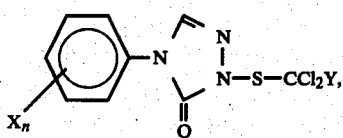
(I)

where X is hydrogen, halogen (eg. fluorine, chlorine, bromine or iodine), alkyl or alkoxy of 1 to 5 carbon atoms which are unsubstituted or substituted by fluorine, chlorine or bromine, alkenyl of 2 to 4 carbon atoms, cyano or nitro, or phenyl or phenoxy which are unsubstituted or substituted by fluorine, chlorine, bromine or alkyl of 1 to 4 carbon atoms, n is an integer from 1 to 5 and Y is fluorine or chlorine, have a powerful fungicidal action. The novel compounds have a broad spectrum of action and may in particular be used to control Phycomycetes and Fungi Imperfecti, but also Ascomycetes and Basidiomycetes. The novel compounds are for example suitable for use in crop protection, for controlling phytopathogenic fungi, eg. *Plasmopara viticola* in vines, *Pseudoperonospora humuli* in hops, *Phytophthora infestans* in potatoes and tomatoes, *Pythium ultimum* in pea seedlings, *Botrytis cinerea* in vines, strawberries and paprika, *Septoria nodorum* in cereals and *Venturia inaequalis* (scab) in apple trees. At the concentrations required to control the fungi, the compounds do not damage crop plants. Furthermore, the novel 1-(trihalomethyl-sulfenyl)-4-aryl-1,2,4-triazolin-5-ones are outstandingly useful for protecting materials and for protecting timber against such species of fungi as Sclerophoma and Pullularia.

Further, we have found that the compounds of the general formula (I) may be obtained by reacting a 4-aryl-1,2,4-triazolin-5-one of the formula (II)

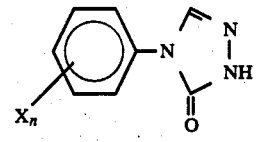
(II)

with a sulfenyl chloride of the formula $YCCl_2-S-Cl$ (III),

X, Y and n having the above meanings, in the presence or absence of an acid acceptor and in the presence or absence of a solvent or diluent. The reaction according to the invention is advantageously carried out in a solvent or diluent which is inert toward the reactants, for example toluene, xylene, diethyl ether, tetrahydrofuran, dioxane, dimethoxyethane, acetone, methyl ethyl ketone, ethyl acetate, methylene chloride, chloroform, dichloroethane or chlorobenzene.

Examples of suitable acid acceptors are inorganic bases, such as hydroxides and carbonates of alkali metals and alkaline earth metals (eg. NaOH, NaHCO$_3$, Na$_2$CO$_3$, KHCO$_3$, K$_2$CO$_3$, CaCO$_3$ and BaCO$_3$) and especially tertiary amines, eg. triethylamine, N,N-dimethyl-cyclohexylamine, N,N-dimethylaniline or pyridine.

The reaction is carried out at, for example, from $-30°$ to $+100°$ C., preferably from $-10°$ to $+25°$ C., under atmospheric pressure.

The novel compounds of the general formula (I), where Y is fluorine, are also obtained when a 1,2,4-triazolin-3-one of the formula Ia

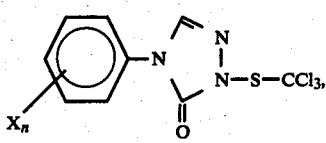
Ia where X and n have the above meanings, is reacted with anhydrous hydrofluoric acid, in order to replace a chlorine in the trichloromethylthio side chain by fluorine. This reaction with a compound of the formula Ia may be carried out in an excess of hydrofluoric acid as the diluent, at from $-50°$ to $+80°$ C., preferably from $-10°$ to $+25°$ C., under atmospheric or super-atmospheric pressure.

The formula (II) provides a general definition of the 4-aryl-1,2,4-triazolin-5-ones to be used as starting materials. In this formula, X is preferably hydrogen, fluorine, chlorine, bromine, methyl, ethyl, isopropyl, tert.-butyl, trifluoromethyl, nitro, methoxy, ethoxy, tetrafluoroethoxy, phenoxy or phenyl, and n is preferably 1, 2, 3 or 4.

Some of the starting compounds of the formula (II) are known (cf. H. Gehlen and W. Schade, Liebigs Ann. Chem., 675 (1964), 180 and M. Pesson and S. Dupin, Bull. Soc. Chim. France (1962), 250). Novel starting materials of the formula (II) can be obtained by the conventional method of cyclizing a 1-aryl-4-formyl-semicarbazide in the presence of an alkali metal hydroxide.

The formula (Ia) provides a general definition of the 1-trichloromethyl-sulfenyl-4-aryl-1,2,4-triazolin-3-ones which are also required for the preparation of the novel compounds. The compounds of the formula (Ia) may be prepared by processes known in principle and employed conventionally in the laboratory. Further information is to be found in the Preparation Examples.

Finally, the trihalomethyl-sulfenyl chlorides of the formula III, also required for the preparation of the novel compounds, are generally known compounds.

Specific examples of the novel active ingredients are 1-trichloromethyl-sulfenyl-4-phenyl-1,2,4-triazolin-5-one, 1-fluorodichloromethyl-sulfenyl-4-phenyl-1,2,4-triazolin-5-one, 1-trichloromethyl-sulfenyl-4-(2-chlorophenyl)-1,2,4-triazolin-5-one, 1-fluorodichloromethyl-sulfenyl-4-(2-chlorophenyl)-1,2,4-triazolin-5-one, 1-trichloromethyl-sulfenyl-4-(3-chlorophenyl)-1,2,4-triazolin-5-one, 1-fluorodichloromethyl-sulfenyl-4-(3-chlorophenyl)-1,2,4-triazolin-5-one, 1-trichloromethylsulfenyl-4-(4-chlorophenyl)-1,2,4-triazolin-5-one, 1-fluorodichloromethyl-sulfenyl-4-(4-chlorophenyl)-1,2,4-triazolin-5-one, 1-trichloromethyl-sulfenyl-4-(2,4-dichlorophenyl)-1,2,4-triazolin-5-one, 1-fluorodichloromethyl-sulfenyl-4-(2,4-dichlorophenyl)-1,2,4-triazolin-5-one, 1-trichloromethyl-sulfenyl-4-(3,4-dichlorophenyl)-1,2,4-triazolin-5-one, 1-fluorodichloromethyl-sulfenyl-4-(3,4-dichlorophenyl)-1,2,4-triazolin-5-one, 1-trichloromethyl-sulfenyl-4-(3,5-dichlorophenyl)-1,2,4-triazolin-5-one, 1-fluorodichloromethyl-sulfenyl-4-(3,5-dichlorophenyl)-1,2,4-triazolin-5-one, 1-trichloromethyl-sulfenyl-4-(2,4,5-trichlorophenyl)-1,2,4-triazolin-5-one, 1-trichloromethyl-sulfenyl-4-(4-fluorophenyl)-1,2,4-triazolin-5-one, 1-fluorodichloromethyl-sulfenyl-4-(4-fluorophenyl)-1,2,4-triazolin-5-one, 1-trichloromethyl-sulfenyl-4-(3,4-difluorophenyl)-1,2,4-triazolin-5-one, 1-trichloromethyl-sulfenyl-4-(4-bromophenyl)-1,2,4-triazolin-5-one, 1-trichloromethyl-sulfenyl-4-(4-methylphenyl)-1,2,4-triazolin-5-one, 1-fluorodichloromethyl-sulfenyl-4-(4-methylphenyl)-1,2,4-triazolin-5-one, 1-trichloromethyl-sulfenyl-4-(2,4-dimethylphenyl)-1,2,4-triazolin-5-one, 1-trichloromethyl-sulfenyl-4-(2-methyl-4-chlorophenyl)-1,2,4-triazolin-5-one, 1-fluorodichloromethyl-sulfenyl-4-(2-methyl-4-chlorophenyl)-1,2,4-triazolin-5-one, 1-trichloromethyl-sulfenyl-4-(3-trifluoromethyl-phenyl)-1,2,4-triazolin-5-one, 1-fluorodichloromethyl-sulfenyl-4-(3-trifluoromethyl-phenyl)-1,2,4-triazolin-5-one, 1-trichloromethylsulfenyl-4-(4-trifluoromethyl-phenyl)-1,2,4-triazolin-5-one, 1-trichloromethyl-sulfenyl-4-(3-nitrophenyl)-1,2,4-triazolin-5-one, 1-fluorodichloromethylsulfenyl-4-(3-nitrophenyl)-1,2,4-triazolin-5-one, 1-trichloromethyl-sulfenyl-4-(4-nitrophenyl)-1,2,4-triazolin-5-one, 1-fluorodichloromethyl-sulfenyl-4-(4-nitrophenyl)-1,2,4-triazolin-5-one, 1-trichloromethylsulfenyl-4-(4-isopropyl-phenyl)-1,2,4-triazolin-5-one, 1-fluorodichloromethyl-sulfenyl-4-(4-isopropyl-phenyl)-1,2,4-triazolin-5-one, 1-trichloromethyl-sulfenyl-4-(4-tert.-butyl-phenyl)-1,2,4-triazolin-5-one, 1-trichloromethyl-sulfenyl-4-(3-tert.-butyl-phenyl)-1,2,4-triazolin-5-one, 1-fluorodichloromethyl-sulfenyl-4-(3-tert.-butyl-phenyl)-1,2,4-triazolin-5-one, 1-trichloromethyl-sulfenyl-4-(4-methoxyphenyl)-1,2,4-triazolin-5-one, 1-fluorodichloromethyl-sulfenyl-4-(methoxy-phenyl)-1,2,4-triazolin-5-one, 1-trichloromethyl-sulfenyl-4-(3-chloro-4-methoxyphenyl)-1,2,4-triazolin-5-one, 1-fluorodichloromethyl-sulfenyl-4-(3-chloro-4-methoxyphenyl)-1,2,4-triazolin-5-one, 1-trifluoromethyl-sulfenyl-4-(3,5-dichloro-4-methoxyphenyl)-1,2,4-triazolin-5-one, 1-fluorodichloromethyl-sulfenyl-4-(3,5-dichloro-4-methoxyphenyl)-1,2,4-triazolin-5-one, 1-trichloromethyl-sulfenyl-4-(3-tetrafluoroethoxy-phenyl)-1,2,4-triazolin-5-one, 1-trichloromethyl-sulfenyl-4-(4-tetrafluoromethoxy-phenyl)-1,2,4-triazolin-5-one, 1-fluorodichloromethyl-sulfenyl-4-(3-tetrafluoroethoxy-phenyl)-1,2,4-triazolin-5-one, 1-fluorodichloromethyl-sulfenyl-4-(4-tetrafluoroethoxy-phenyl)-1,2,4-triazolin-5-one, 1-trichloromethyl-sulfenyl-4-[4-(4'-chlorophenoxy)-phenyl]-1,2,4-triazolin-5-one, 1-fluorodichloromethyl-sulfenyl-4-[4-(4'-chlorophenoxy)-phenyl]-1,2,4-triazolin-5-one, 1-trichloromethyl-sulfenyl-4-(4-biphenylyl)-1,2,4-triazolin-5-one and 1-fluorodichloromethyl-sulfenyl-4-(4-biphenylyl)-1,2,4-triazolin-5-one.

The experiments which follow illustrate the preparation of the active ingredients.

PREPARATION EXAMPLES

Example 1

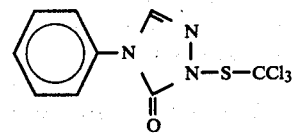

19 g (0.102 mole) of perchloromethylmercaptan and 10 g (0.099 mole) of triethylamine are successively added dropwise, at from about 10° to 15° C., to a well-stirred suspension of 16.1 g (0.1 mole) of 4-phenyl-1,2,4-triazolin-5-one in 150 ml of dry ethyl acetate. After having stirred the mixture for two hours at room temperature (20° C.), the triethylamine hydrochloride which has precipitated is filtered off and washed with 40 ml of ethyl acetate. The filtrate is washed by shaking with 2×100 ml of water, and is dried over Na₂SO₄, after which the solvent is evaporated. The residue crystallizes at 0° C. after addition of 20 ml of ether.

25.8 g (83% of theory) of 1-trichloromethyl-sulfenyl-4-phenyl-1,2,4-triazolin-5-one are obtained as white crystals of melting point 169°–171° C. (No. 1).

Example 2

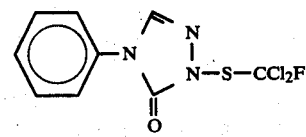

Following a procedure similar to Example 1, 16.1 g (0.1 mole) of 4-phenyl-1,2,4-triazolin-5-one are reacted with 17 g (0.1 mole) of fluorodichloromethyl-sulfenyl chloride. 20.9 g (76% of theory) of 1-fluorodichloromethyl-sulfenyl-4-phenyl-1,2,4-triazolin-5-one are obtained as white crystals of melting point 128°–130° C. (No. 2).

The following compounds of the formula I were prepared by a similar method and were characterized by infrared and nuclear resonance spectroscopy, as well as by elementary analysis.

TABLE

| Example No. | X | X | Melting point °C. |
|---|---|---|---|
| 3 | 4-Cl | Cl | 174–178 |
| 4 | 4-Cl | F | 151–153 |
| 5 | 3-Cl | Cl | 155–158 |
| 6 | 3-Cl | F | 118–120 |
| 7 | 3,5-Cl₂ | Cl | 187–190 |

TABLE-continued

| Example No. | X | X | Melting point °C. |
|---|---|---|---|
| 8 | 4-F | Cl | 145–147 |
| 9 | 4-F | F | 113–115 |
| 10 | 3-F$_3$C— | Cl | 150–153 |
| 11 | 3-F$_3$C— | F | 111–116 |
| 12 | 2-CH$_3$—, 4-Cl | Cl | 84–87 |
| 13 | 2-CH$_3$, 4-Cl | F | Resin |
| 14 | 3-Cl, 4-OCH$_3$ | Cl | 198–200 |
| 15 | 3-Cl, 4-OCH$_3$ | F | 152–155 |
| 16 | 4-OCH$_3$ | Cl | 161–163 |
| 17 | 3-tert.—C$_4$H$_9$ | Cl | 163–165 |
| 18 | 3-tert.—C$_4$H$_9$ | F | 142–144 |
| 19 | 4-OCH$_3$ | F | 114–116 |

The novel compounds are exceptionally active against a broad spectrum of phythopathogenic fungi. They may be used as leaf fungicides and soil fungicides.

In particular, the novel compounds are suitable for control of the following plant diseases: *Phytophthora infestans* in tomatoes and potatoes, *Phytophthora parasitica* in strawberries, *Phytophthora cactorum* in apples, *Pseudoperonspora cubensis* in cucumbers, *Pseudoperonospora humuli* in hops, *Peronospora destructor* in onions, *Peronospora sparsa* in roses, *Peronospora tabacina* in tobacco, *Plasmopara viticola* in vines, *Plasmopara halstedii* in sunflowers, *Pythium ultimum* in pea seedlings, *Botrytis cinerea* in vines, strawberries and paprika, *Septoria nodorum* in cereals and *Venturia inaeqalis* (scab) in apple trees.

The compounds are employed by spraying or dusting the plants with them or treating the seeds of the plants with them. They may be used before or after infection of the plants or seed by the fungi.

The novel compounds can be converted to the conventional formulations, such as solutions, emulsions, suspensions, dusts, powders, pastes and granules. The form depends entirely on the intended use but should in every case ensure fine and uniform distribution of the active ingredient. The formulations are prepared in a conventional manner, for example by extending the active ingredient with solvents and/or carriers, with or without emulsifiers and dispersants; if water is used as the diluent, organic solvents may be present as auxiliary solvents. Essentially, the various auxiliaries employed are solvents, such as aromatics (eg. xylene or benzene), chloroaromatics (eg. chlorobenzenes), paraffins (eg. petroleum fractions), alcohols (eg. methanol or butanol), amines (eg. ethanolamine), dimethylformamide, and water; carriers, such as natural rock powders, eg, kaolins, aluminas, talc and chalk, and synthetic rock powders (eg. finely disperse silica and silicates); emulsifiers, such as non-ionic and anionic emulsifiers (eg. polyoxyethylene-fatty alcohol ethers, alkylsulfonates and arylsulfonates) and dispersants, eg. lignin, sulfite waste liquors and methylcellulose.

The fungicides in general contain from 0.1 to 95, preferably from 0.5 to 90, % by weight of active ingredient.

The amounts applied depend on the nature of the desired effect and are from 0.1 to 3 kg or more of active ingredient per hectare. The novel compounds can also be employed in the protection of materials. When used for such purposes, for example as a fungicide in paints and plasticized polyvinyl chloride, the amounts used are from 0.05 to 5% by weight of active ingredient, based on total weight of the paint to be preserved or of the polyvinyl chloride to be rendered microbicidal. The novel active ingredients can also be employed as fungicidal constituents of oily formulations for protecting timber against fungi which have a discoloring action. The timber is treated with such formulations by, for example, impregnation or brushing.

The fungicides and the ready-to-use formulations prepared therefrom, such as solutions, emulsions, suspensions, powders, dusts, pastes or granules are employed in a conventional manner, for example by spraying, atomizing, dusting, broadcasting, dressing or watering.

The following are some examples of suitable formulations:

I. 90 parts by weight of the compound of Example 1 are mixed with 10 parts by weight of N-methyl-α-pyrrolidone; a solution suitable for use in the form of minute droplets is obtained.

II. 10 parts by weight of the compound of Example 2 are dissolved in a mixture of 90 parts by weight of xylene, 6 parts by weight of an adduct of 8 to 10 moles of ethylene oxide with 1 mole of oleic acid N-monoethanolamide, 2 parts by weight of calcium dodecylbenzenesulfonate and 2 parts by weight of an adduct of 40 moles of ethylene oxide with 1 mole of castor oil.

III. 20 parts by weight of the compound of Example 3 are dissolved in a mixture of 60 parts by weight of cyclohexanone, 30 parts by weight of isobutanol and 10 parts by weight of an adduct of 1 mole of castor oil and 40 moles of ethylene oxide. The solution is poured into 100,000 parts by weight of water and finely distributed therein, giving an aqueous dispersion containing 0.02% by weight of the active ingredient.

IV. 20 parts by weight of the compound of Example 5 are dissolved in a mixture of 25 parts by weight of cyclohexanone, 65 parts by weight of a mineral oil fraction of boiling point 210°–280° C. and 10 parts by weight of an adduct of 1 mole of castor oil and 40 moles of ethylene oxide. The solution is poured into 100,000 parts by weight of water and finely distributed therein, giving an aqueous dispersion containing 0.02% by weight of the active ingredient.

V. 80 parts by weight of the compound of Example 2 are thoroughly mixed with 3 parts by weight of sodium diisobutylnaphthalene-α-sulfonate, 10 parts by weight of the sodium salt of a ligninsulfonic acid from a sulfite waste liquor and 7 parts by weight of silica gel powder, and the mixture is milled in a hammer mill. On finely dispersing the mixture in 20,000 parts by weight of water, a spray liquor containing 0.1% by weight of the active ingredient is obtained.

VI. 3 parts by weight of the compound of Example 6 are intimately mixed with 97 parts by weight of finely divided kaolin. A dust containing 3% by weight of active ingredient is obtained.

VII. 30 parts by weight of the compound of Example 1 are intimately mixed with 92 parts by weight of silica gel powder onto whose surface 8 parts by weight of paraffin oil have first been sprayed. The resulting formulation of the active ingredient possesses good adherence.

VIII. 40 parts by weight of the compound of Example 3 are intimately mixed with 10 parts of the sodium salt of a phenolsulfonic acid/urea/formaldehyde condensate, 2 parts of silica gel and 48 parts of water. A stable aqueous dispersion is obtained, which on dilution with 100,000 parts by weight of water gives a dispersion containing 0.04% by weight of active ingredient.

IX. 20 parts of the compound of Example 1 are intimately mixed with 2 parts of calcium dodecylbenzenesulfonate, 8 parts of a fatty alcohol polyglycol ether, 2 parts of the sodium salt of a phenolsulfonic acid/urea/formaldehyde condensate and 68 parts of a paraffinic mineral oil. A stable oily dispersion is obtained.

The above use forms of the novel agents can additionally contain other active ingredients, for example herbicides, insecticides, growth regulators or other fungicides, and can also be mixed with fertilizers and applied as such mixers. If mixed with other fungicides, the resulting formulation in many cases has a broader fungicidal spectrum of action.

The list, given below, of fungicides with which the novel compounds can be combined is intended to illustrate the possibilities without implying a limitation to the Examples given.

Examples of fungicides which can be combined with the novel compounds are: sulfur; dithiocarbamates and their derivatives, such as iron(III) dimethyldithiocarbamate, zinc dimethyldithiocarbamate, manganese-zinc ethylenediamine-bis-dithiocarbamate, zinc ethylene-bis-dithiocarbamate, tetramethylthiuram disulfides, the ammonia complex of zinc N,N-ethylene-bis-dithiocarbamate and N,N'-polyethylene-bis-(thiocarbamyl)-disulfide, zinc N,N'-propylene-bis-dithiocarbamate, and the ammonia complex of zinc N,N'-propylene-bis-dithiocarbamate and N,N'-polypropylene-bis-(thiocarbamyl)-disulfide; nitro derivatives, eg. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, eg. N-(1,1,2,2-tetrachloroethylthio)-tetrahydrophthalimide, N-trichloromethylthio-tetrahydrophthalimide, 2-heptadecyl-imidazoline-acetate, 2,4-dichloro-6-(o-chloroanilino)-s-triazine, 0,0-diethylphthalimidophosphonothioate, 5-amino-1-(bis-(dimethylamino)-phosphinyl)-3-phenyl-1,2,4-triazole, 2,3-dicyano-1,4-dithioanthraquinone, 2-thio-1,3-dithio-(4,5-b)-quinoxaline, methyl 1-(butylcarbamyl)-benzimidazole-2-carbamate, 4-(2-chlorophenylhydrazono)-3-methyl-5-isoxazolone, pyridine-2-thiol-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathiine, 2-(fur-2-yl)-benzimidazole, piperazine-1,4-diyl-bis-(1-(2,2,2-trichloroethyl)-formamide), 2-(thiazol-4-yl)-benzimidazole, 5-butyl-2-dimethylamino-4-hydroxy-6-methyl-pyrimidine, bis-(p-chlorophenyl)-(pyridin-3-yl)-methanol, 1,2-bis-(3-ethoxycarbonyl-2-thioureido)-benzene and 1,2-bis-(3-methoxycarbonyl-2-thioureido)-benzene; as well as various fungicides such as dodecylguanidine acetate, 3-(3,5-dimethyl-2-hydroxy-cyclohexyl)-2-hydroxyethyl-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, 1-(4-chlorophenoxy)-3,3-dimethyl-1-(1H-1,2,4-triazol-1-yl)-butan-2-one, 1-(4-chlorophenoxy)-3,3-dimethyl-1-(1H-1,2,4-triazol-1-yl)-butan-2-ol and α-(2-chlorophenyl)-α-(4-chlorophenyl)-(pyrimidin-5-yl)-methanol.

In the experiments below, the following conventional active ingredients were used as comparative agents:

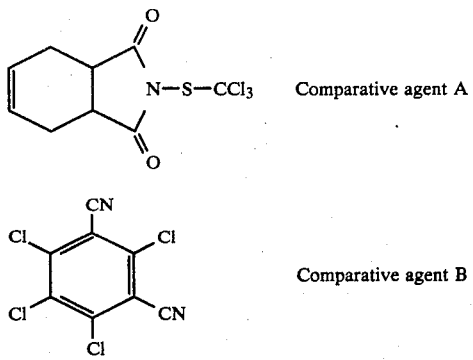

Comparative agent A

Comparative agent B

EXPERIMENT 1

Activity against *Phytophthora infestans* in tomatoes

Leaves of pot-grown plants of tomatoes, Grosse Fleischtomate variety, are sprayed with aqueous suspensions containing 0.025% by weight of active ingredient. When the sprayed film has dried, the leaves are infected with a zoospore suspension of the fungus *Phytophthora infestans*. The plants are then placed in a chamber at 100% atmospheric humidity, at from 16° to 18° C. After 5 days, the disease has developed sufficiently strongly on the untreated, but infected control plants for the fungicidal activity of the substances to be assessed.

The novel compounds 1, 3, 4, 5, 6 and 7 showed a greater fungicidal activity than the conventional compound A.

EXPERIMENT 3

*Septoria nodorum* in wheat

Leaves of pot-grown wheat plants, Jubilar variety, are sprayed to run-off with aqueous spray liquors containing 0.05 or 0.1% by weight of emulsified active ingredient. When the sprayed film has dried, the plants are sprayed with a spore suspension of the fungus *Septoria nodorum* and are placed in a chamber at high atmospheric humidity, at from 16° to 18° C., in order to provide optimum conditions for the fungus to develop. After 14 days, the disease has developed sufficiently strongly on the untreated control plants that the leaf spots formed cover the greater part of the leaves.

The novel compounds, 1, 5 and 6 showed a greater fungicidal activity than the conventional compound B.

We claim:

1. A 1-(trihalomethyl-sulfenyl)-4-aryl-1,2,4-triazolin-5-one of the general formula

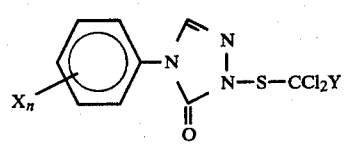

where X is hydrogen, halogen, alkyl or alkoxy of 1 to 5 carbon atoms which are unsubstituted or substituted by fluorine, chlorine or bromine, alkenyl of 2 to 4 carbon atoms, cyano or nitro, or phenyl or phenoxy which are unsubstituted or substituted by fluorine, chlorine, bromine or alkyl of 1 to 4 carbon atoms, n is an integer from 1 to 5 and Y is fluorine or chlorine.

2. A method for controlling fungi, wherein the fungus or the object to be protected from fungal attack is treated with a 1-(trihalomethyl-sulfenyl)-4-aryl-1,2,4-triazolin-5-one of the general formula

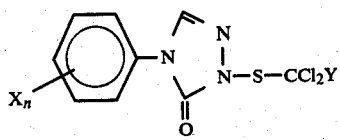

where X is hydrogen, halogen, alkyl or alkoxy of 1 to 5 carbon atoms which are unsubstituted or substituted by fluorine, chlorine or bromine, alkenyl of 2 to 4 carbon atoms, cyano or nitro, or phenyl or phenoxy which are unsubstituted or substituted by fluorine, chlorine, bromine or alkyl of 1 to 4 carbon atoms, n is an integer from 1 to 5 and Y is fluorine or chlorine.

3. A compound as claimed in claim 1, selected from the group comprising 1-trichloromethyl-sulfenyl-4-phenyl-1,2,4-triazolin-5-one, 1-trichloromethyl-sulfenyl-4-(3-chlorophenyl)-1,2,4-triazolin-5-one, 1-fluorodichloromethyl-sulfenyl-4-(3-chlorophenyl)-1,2,4-triazolin-5-one, 1-trichloromethyl-sulfenyl-4-(4-chlorophenyl)-1,2,4-triazolin-5-one, 1-fluorodichloromethyl-sulfenyl-4-(4-chlorophenyl)-1,2,4-triazolin-5-one, 1-trichloromethyl-sulfenyl-4-(4-fluorophenyl)-1,2,4-triazolin-5-one, 1-fluorodichloromethyl-sulfenyl-4-(4-fluorophenyl)-1,2,4-triazolin-5-one, 1-trichloromethyl-sulfenyl-4-(3,5-dichlorophenyl)-1,2,4-triazolin-5-one, 1-trichloromethyl-sulfenyl-4-(3-trifluoromethyl-phenyl)-1,2,4-triazolin-5-one, 1-fluorodichloromethyl-sulfenyl-4-(3-trifluoromethyl-phenyl)-1,2,4-triazolin-5-one, 1-trichloromethyl-sulfenyl-4-(2-methyl-4-chlorophenyl)-1,2,4-triazolin-5-one, 1-fluorodichloromethyl-sulfenyl-4-(2-methyl-4-chlorophenyl)-1,2,4-triazolin-5-one, 1-trichloromethyl-sulfenyl-4-(3-chloro-4-methoxyphenyl)-1,2,4-triazolin-5-one, 1-trichloromethyl-sulfenyl-4-(4-methoxyphenyl)-1,2,4-triazolin-5-one, 1-fluorodichloromethyl-sulfenyl-4-(4-methoxyphenyl)-1,2,4-triazolin-5-one and 1-trichloromethyl-sulfenyl-4-(3-tert.-butyl)-1,2,4-triazolin-5-one.